United States Patent [19]
Hariharan et al.

[11] Patent Number: 5,916,968
[45] Date of Patent: Jun. 29, 1999

[54] ADHESIVES RESISTANT TO SKIN-PENETRATION ENHANCERS

[75] Inventors: Deepak Hariharan, Somerville, N.J.; Roman Bradel, Kingwood, Tex.; Rama Chandran, Brigdewater; Pravin Kukkala, Raritan, both of N.J.

[73] Assignee: National Starch and Chemical Investment Holding Corporation, Wilmington, Del.

[21] Appl. No.: 08/918,173

[22] Filed: Aug. 25, 1997

Related U.S. Application Data

[62] Division of application No. 08/599,428, Jan. 17, 1996, abandoned.

[51] Int. Cl.$^6$ .......................... C09J 105/00; C09J 133/08
[52] U.S. Cl. .................. 525/54.2; 525/54.23; 525/54.26; 525/183; 525/187; 525/217; 527/314; 424/448; 424/449
[58] Field of Search ................................ 525/54.2, 54.23, 525/54.26; 527/314; 424/448, 449

[56] References Cited

U.S. PATENT DOCUMENTS

| | | | |
|---|---|---|---|
| Re. 24,906 | 12/1960 | Ulrich | 206/59 |
| 3,786,116 | 1/1974 | Milkovich et al. | 260/885 |
| 3,975,570 | 8/1976 | Ono | 527/314 |
| 4,554,324 | 11/1985 | Husman et al. | 525/301 |
| 4,656,213 | 4/1987 | Schlademan | 524/272 |
| 4,693,776 | 9/1987 | Krampe et al. | 156/327 |
| 4,732,808 | 3/1988 | Krampe et al. | 428/355 |
| 4,769,028 | 9/1988 | Hoffmann | 424/443 |
| 4,851,278 | 7/1989 | Enanoza | 428/195 |
| 4,871,812 | 10/1989 | Lucast et al. | 525/186 |
| 4,931,347 | 6/1990 | Slovinsky et al. | 428/192 |
| 4,981,903 | 1/1991 | Garbe | 524/547 |
| 4,994,322 | 2/1991 | Delgado et al. | 428/343 |
| 5,006,582 | 4/1991 | Mancinelli | 524/271 |
| 5,021,477 | 6/1991 | Garbe et al. | 424/70 |
| 5,032,637 | 7/1991 | Therriault et al. | 524/375 |
| 5,143,972 | 9/1992 | Groves | 525/71 |
| 5,223,261 | 6/1993 | Nelson et al. | 424/443 |
| 5,232,702 | 8/1993 | Pfister et al. | 424/448 |
| 5,266,402 | 11/1993 | Delgado et al. | 428/355 |
| 5,288,827 | 2/1994 | Li | 526/279 |
| 5,352,516 | 10/1994 | Therriault et al. | 428/355 |
| 5,387,450 | 2/1995 | Stewart | 428/40 |
| 5,387,466 | 2/1995 | Therriault et al. | 428/355 |
| 5,393,529 | 2/1995 | Hoffmann et al. | 424/445 |
| 5,536,778 | 7/1996 | Kreckel | 524/13 |

FOREIGN PATENT DOCUMENTS

| | | |
|---|---|---|
| 0 403 197 A2 | 12/1990 | European Pat. Off. . |
| 0 571 991 A1 | 12/1993 | European Pat. Off. . |
| 0 622 075 A1 | 11/1994 | European Pat. Off. . |
| 43 01 783 C1 | 3/1994 | Germany . |
| 125753 | 8/1982 | Japan ..................... 424/448 |
| 123416 | 7/1985 | Japan . |
| 123417 | 7/1985 | Japan . |
| 61-033114 | 2/1986 | Japan . |
| 1495845 | 12/1977 | United Kingdom . |
| WO 84/03837 | 10/1984 | WIPO . |
| WO 86/06281 | 11/1986 | WIPO . |
| WO 95/02003 | 1/1995 | WIPO . |
| WO 95/14746 | 6/1995 | WIPO . |

OTHER PUBLICATIONS

Sarat C. Chattaraj and Roderick B. Walker, "Penetration Enhancer Classification", 1995, CRC Press, Inc., pp. 5–15.

Steven M. Wick, R. Ph., "Developing A Drug–In–Adhesive Design For Transdermal Drug Deliver", *Adhesives Age*, Sep. 1995, pp. 18–24.

*Primary Examiner*—David Buttner
*Attorney, Agent, or Firm*—Jane E. Gennaro; Lydia T. McNally

[57] ABSTRACT

A graft copolymer for use as an adhesive for drug delivery patches or dressings that is resistant to dissolution in the presence of skin penetration enhancers comprises copolymerized acrylic and, optionally, vinyl monomers, to form a backbone polymer, to which are grafted polymeric moieties that do not absorb greater than 3% by weight of a skin-penetration enhancer under thermodynamic equilibrium at 25° C. if independently introduced into an excess of the enhancer. Preferably, the grafted polymers are selected from the classes of polybutylene, polysaccharide, poly(ethyleneoxide/propyleneoxide), and polyamide polymers, and specific grafted polymers will depend on the specific enhancers used in a particular drug delivery system.

2 Claims, No Drawings

ADHESIVES RESISTANT TO SKIN-PENETRATION ENHANCERS

This application is a division of application Ser. No. 08/599,428, filed Jan. 17, 1996 now abandoned.

FIELD OF THE INVENTION

This invention relates to pressure sensitive adhesives for use with wound dressings or transdermal drug delivery systems in which the adhesives are resistant to plasticization by skin penetration enhancers contained in the drug formulation.

BACKGROUND OF THE INVENTION

A typical transdermal drug delivery or wound dressing system comprises a flexible backing on which are applied either as one layer or in spatial separation: a pressure sensitive adhesive, the desired drug, and, particularly in the case of the transdermal systems, a skin-penetration enhancer for the drug. The enhancers useful in transdermal drug delivery applications are well documented and fall into the categories of sulfoxides, alcohols, fatty acids, fatty acid esters, polyols, polyamides, and surfactants.

Historically, the adhesives used for transdermal drug delivery fall into one of three categories: acrylics, silicones and rubbers. Silicone based adhesives have a long history of use on skin because of their purity and low tendency to cause skin irritation. However, their non-polar nature limits the loading of polar drugs into the adhesive and the chemistry renders the composition relatively inflexible. Rubber based adhesives on the other hand are more flexible, but need to be formulated with relatively high amounts tackifiers and plasticizers to provide pressure sensitive properties, and antioxidants to improve stability upon exposure to light (UV). The presence of such high levels of low molecular weight additives leads to skin irritation and presents the danger of the additives penetrating the skin barrier. Rubber based adhesives are also non-polar and thus limit the loading of functional drugs into the adhesive.

In comparison to silicones and rubber adhesives, acrylic adhesives offer a number of advantages: the chemistry is easily manipulated to permit the synthesis of both polar and non-polar adhesives; conventional synthetic techniques can be used; compositions can be tailored to give specific properties without the use of any added ingredients; they are UV stable and can be stored for extended periods of time; and most drugs are more readily soluble in acrylic adhesives than in silicones and rubbers, which allows a higher loading of drug into a smaller patch size and serves to improve patient compliance.

Despite these advantages, acrylic adhesives are highly compatible or soluble in the commonly used skin penetration enhancers compared to the relatively inert silicones and rubbers. This compatibility limits the loading of enhancer and, consequently, the capability of the system to deliver optimum levels of the desired drugs. It also, over time, causes the acrylic adhesive to plasticize to such an extent that it disintegrates with a loss of cohesive and adhesive properties.

Attempts have been made to counteract this dissolution by increasing the level of crosslinking in the adhesive or by grafting polymers, such as polystyrene, with higher Tg values onto the acrylic polymeric chain. However, high crosslinking results in inflexible adhesives, and as the enhancer becomes depleted by absorption into the skin, the presence of the high Tg polystyrene grafts causes a loss in pressure sensitive properties.

In addition to problems with the compositions of the adhesives, the techniques for making the graft and block copolymers with acrylic backbone also present problems. Techniques described in the literature include polymerization of the grafted moiety from a site, such as a hydroxyl group, on the backbone polymer using peroxides as free radical initiators, or the use of macromonomers (as the grafted moiety) with a terminal double bond as a monomer during polymerization. The use of peroxides to initiate a polymerization from sites on the backbone results in uncontrolled grafting in terms of frequency and length of grafts. Uncontrolled grafting produces a polymer with morphologies that do not give optimum cohesion (because of low molecular weight homopolymer formation) or produces low molecular weight grafts that do not provide any reinforcement in the presence of enhancers. The use of macromers during a free radical polymerization is inefficient, results in high residual monomers, and early chain termination because of the large number of terminating sites available on the grafts.

It would be an advantage to provide an adhesive, suitable for use in a wound dressing or transdermal drug delivery system, that maintains its pressure sensitive properties and does not dissolve in the commonly used skin-penetration enhancers over time and through use.

The objects of this invention are to provide a pressure sensitive acrylic polymer with sufficient cohesion and adhesion for use in transdermal drug delivery systems that is insoluble in the commonly used enhancers, and thus will maintain its adhesive and cohesive strength over time.

SUMMARY OF THE INVENTION

The objects of this invention are achieved through a graft copolymer, having a weight average molecular weight of 300,000 or greater, that demonstrates good performance on skin in the presence of skin-penetration enhancers without extensive crosslinking or high Tg grafts. The graft copolymer comprises copolymerized acrylic and, optionally, vinyl monomers, to form a backbone polymer, to which are grafted polymeric moieties that absorb less than 10% by weight of a skin-penetration enhancer under thermodynamic equilibrium at 25° C. if independently introduced into an excess of the enhancer. Preferably, the grafted polymers are selected from the classes of polybutylene, poly (ethyleneoxide/propyleneoxide)s, polycaprolactam, polysaccharide, and polyamide polymers. Specific grafted polymers will depend on the specific enhancers used in a particular drug delivery or wound dressing system inasmuch as different erhancers will present different solubility considerations for the adhesives.

The preferred grafting technique comprises separately performing the acrylic/vinyl backbone and the enhancer resistant polymer and then grafting the enhancer resistant polymer onto the acrylic/vinyl backbone.

DETAILED DESCRIPTION OF THE INVENTION

The acrylic/vinyl polymeric backbone is synthesized from those known acrylic and vinyl monomers in weight proportion to give a glass transition temperature of −30° C. or lower and the desired pressure sensitive cohesive and adhesive properties for the particular transdermal application. In addition, the polymeric backbone will also be synthesized from 0.5–2.0% by weight of a functionalized vinyl monomer containing a polymerizable vinyl group and a second functional group that is capable of being reacted in a condensation reaction with a third functionality on the preferred polymers that are to be grafted onto the polymeric backbone. Preferably, the functional monomers will be 2-isocyanato ethyl methacrylate, allyl isocyanate, and more preferably, will be 1-(1-isocyanato-1-methyl ethyl)-3-(1-methyl ethenyl)benzene (hereinafter, m-TMI), which introduce pendant isocyanate functionality to the polymeric backbone.

Although other grafting techniques are known, for example, polymeric moieties may be grafted by polymerizing monomer onto reactive sites located on the backbone or by copolymerizing the acrylic and vinyl monomers with preformed polymeric monomer, the preferred grafting technique comprises attaching preformed polymeric moieties to sites on the preformed backbone via a condensation reaction. This preferred grafting technique permits the graft of previously synthesized polymers that have substantially the same molecular weight, and allows predetermination of the grafting distribution by control of the amount of m-TMI copolymerized into the backbone polymer. This technique also results in lower levels of monomer residuals in the final graft polymers.

The polymeric acrylic/vinyl backbone is prepared from those known acrylic and vinyl monomers, in the weight proportion required to give the proper balance of pressure sensitive properties. Exemplary acrylic monomers include α,β-unsaturated mono- and dicarboxylic acids having 3–5 carbon atoms, such as acrylic acid, methacrylic acid, and itaconic acid; acrylate ester monomers selected from the group consisting of the alkyl esters of acrylic and methacrylic acid in which the alkyl groups contain 4 to 14 carbon atoms, preferably 4 to 8 carbon atoms, such as, n-butyl acrylate, n-pentyl acrylate, n-hexyl acrylate, n-heptyl acrylate, n-octyl acrylate, n-nonyl acrylate, and their corresponding branched isomers, such as, 2-ethylhexyl acrylate.

Exemplary vinyl monomers include those selected from the groups consisting of vinyl esters, vinyl ethers, vinyl halides, vinylidene halides, and include, for example, vinyl acetate, acrylamide, t-octyl acrylamide, ethyl vinyl ether, vinyl chloride, vinylidene chloride, acrylonitrile, maleic anhydride and styrene.

In addition to the acrylic and vinyl monomers, the backbone polymer will also be synthesized from a monomer having a vinyl functionality, which will react in the polymerization process, and a second functionally unreactive in the polymerization, but capable of reacting in a condensation reaction as the site for attaching the polymers to be grafted to the backbone. The preferred dual functional monomer will be m-TMI, and will be incorporated at a level of 0.5–2% by weight of the backbone polymer.

The preparation of the polymeric backbone can be carried out by mixing the monomers together with initiator under inert atmosphere using well-known free-radical solution, emulsion, or bulk polymerization procedures. After the polymerization is complete, the pendant functionality on the polymer chain is reacted in a condensation reaction with the polymer to be grafted, which will be selected or prepared to have a functional group reactive with the pendant functionality on the polymer backbone. When m-TMI is incorporated, the site for attaching the pendant grafts is the isocyanate functionality, and the preformed grafts will have, for examples, hydroxyl or amine functional groups.

The polymers to be grafted will be insoluble in an excess of drug enhancer to the extent that they absorb ten percent or less by weight of the enhancer under thermodynamic equilibrium at 25° C. In an ideal situation, the graft polymers will absorb 0% of the enhancer. In practice, it is known that polymers that absorb 10% or greater of the enhancer by weight will disintegrate in the presence of the enhancer. Therefore, practicably, suitable polymers will absorb by weight of the enhancer, less than 10%, preferably less than 7%, and more preferably less than 3%.

Representative commercially available polymers for grafting to the acrylic/vinyl chain are amine-terminated saccharides from National Starch and Chemical Co., Bridgewater, N.J.; polybutylenes, sold under the tradename Kraton by Shell Chemical Company, Houston, Tex.; poly (ethyleneoxide/propyleneoxide) monoamines, sold under the tradename Jeffamine by Huntsman Corporation, Houston, Tex.; polyaimides, sold under the tradename Uni-Rex by Union Camp Corporation, Jacksonville, Fla.; and polycaprolactams, sold under the tradename Ultramid, by BASF Corporation, Parsippany, N.J.

The polysaccharide grafts provide the added advantage of being biocompatible and partially biodegradable. Poly (ethyleneoxide/propyleneoxide) monoamines provide the advantage of having higher water vapor transmission rates than other polymers for grafting. These properties, the biocompatibility and the good water vapor transmission rates are especially desirable in transdermal drug delivery systems and wound dressings.

Other polymers suitable for grafting onto the backbone polymer include homopolymers of vinyl esters, such as, poly(vinyl acetate), poly(vinyl propionate), poly(vinyl pivalate), homopolymers of vinyl halides such as poly(vinyl chloride), poly(vinyledyne chloride) etc.; hompolymers of N-vinyl amides, such as poly-(n-vinyl formamide), poly(n-vinyl acetafnide), poly(n-vinyl pyrrolidone), poly-(n-vinyl caprolactum) etc.; amides such as poly(acrylamide), poly (methacrylamide), poly(dimethyl acrylamine); homopolymers of vinyl ethers such as, poly(sopropyl vinyl ether), poly(butyl vinyl ether) etc.; polyesters, such as poly (ethylene terephthalate), poly(ethylene phthalate), poly (ethylene isophthalate) etc.; and polycarbonates, such as, poly(4,4 methylenediphenylene carbonate) etc.

The graft polymers are typically recovered as lacquers and are coated onto a porous supporting backing material having the ability to absorb moisture and provide integrity for the adhesive. Examples of such materials are knitted, woven, and non-woven fabrics comprised of natural or synthetic materials.

The resultant graft polymers have good skin adhesion aid cohesion, and are stable in the presence of skin penetration enhancers. The following examples describe the polymerization procedures for representative acrylic/vinyl polymers and the grafting of the enhancer resistant polymers, the analytical test methods, and the results of tests measuring cohesive and adhesive strength for the graft copolymers.

EXAMPLES

Example I

Preparation of Base Polymer for Examples A–P and R–Z

The reaction equipment consisted of a five-liter reaction vessel equipped with a thermometer, reflux condenser, $N_2$ inlet, mechanical stirrer, and addition funnels. A mix of monomers (hereinafter Monomer) was prepared to contain by weight 45.5 parts butyl acrylate, 32.5 parts 2-ethyl hexyl acrylate, and 20.55 parts methyl methacrylate. By weight 3.55 parts Monomer, 1.45 parts m-TMI and 0.004 parts azobisisobutyronitrile (initiator) in 16.5 parts ethyl acetate and 16.5 parts hexane, were charged to the reaction vessel under nitrogen and heated with agitation (275 rpm) to reflux and held for ten minutes at 65° C. Nitrogen flow was discontinued when reflux started. Monomer, 95 parts, was added uniformly over two hours. Thirty minutes after the start of the Monomer addition, initiator (0.076 parts) in 26 parts ethyl acetate and 26 parts hexane, was added uniformly over seven hours. At completion of the initiator addition, agitation was increased (300 rpm) and the reaction held at reflux for 30 minutes. Scavenger, t-amyl peroxypivalate, 0.667 parts in 7.5 parts ethyl acetate and 7.5 parts hexane, was then added uniformly over four hours. When addition was complete, the agitation was increased to 400 rpm and the reaction contents Weld at reflux 68° C. for one hour. The isocyanate containing reaction product was cooled to room temperature while purging the reaction vessel with nitrogen. The result was a lacquer, which could be stored at room temperature for up to one week.

Example II
Preparation of Graft Copolymer for Examples A–P and R–Z

A polybutylene, polyamide, or poly(ethylene oxide/propylene oxide) polymer, terminated with hydroxy or amine groups (or both) was grafted to the acrylic base polymer by reaction of the hydroxy or amine groups with the pendant isocyanate on the acrylic/vinyl polymer of Example I to form a urethane or urea linkage. (During the grafting of the polybutylene polymer, a small amount of aminobutanol was also attached to the acrylic/vinyl polymer to introduce hydroxyl groups into the system to promote skin adhesion.)

The polymer to be grafted, 7.453 parts by weight, was diluted with 82.886 parts hexane (ethyl acetate for poly (ethylene oxide/propylene oxide)), and added to a reaction vessel containing the acrylic/vinyl polymer. The reaction contents were heated to reflux and held for six hours. For poly(ethylene oxide/propylene oxide), the reaction contents were heated to reflux and held for ten minutes; the catalyst, 0.167 parts dibutyltindilaurate was added in one charge, and the reaction held at reflux for four hours. 2-Amino-1-butanol, 0.443 parts, was added in one charge and the reaction held at reflux for 30 minutes. (The dibutyltindilaurate catalyst was omitted in reactions involving an amine with the isocyanate groups.) Isopropanol, 16.667 parts, was added in one charge to quench any excess isocyanate and the reaction held at reflux for one hour. The contents were cooled to room temperature and recovered as a lacquer.

Example III
Preparation of Base Polymer for Example Q

The reaction equipment consisted of a five-liter reaction vessel equipped with a thermometer, reflux condenser, $N_2$ inlet, mechanical stirrer, and addition funnels. A mix of monomers (hereinafter Monomer) was prepared to contain by weight 136.5 parts butyl acrylate, 97.5 parts 2-ethyl hexyl acrylate, and 57.0 parts methyl methacrylate. By weight 42.0 parts Monomer, 9.0 parts m-TMI and 0.34 parts t-amyl peroxypivalate (t-APP)(initiator) in 75 parts acetone, were charged to the reaction vessel under nitrogen and heated with agitation (275 rpm) to reflux and held for ten minutes at 65° C. Nitrogen flow was discontinued when reflux started. Monomer, 249 parts, was added uniformly over two hours. Thirty minutes after the start of the Monomer addition, t-APP (initiator) (1.72 parts) in 165 parts acetone, was added uniformly over three hours. At completion of the initiator addition, agitation was increased (300 rpm) and the reaction held at reflux for two hours. The isocyanate containing reaction product was cooled to room temperature while purging the reaction vessel with nitrogen. The result was a lacquer, which could be stored at room temperature for up to one week.

Example IV
Preparation of Graft Copolymer for Example Q

An amine terminated polysaccharide was grafted to the acrylic base polymer by reaction of the terminal amine groups with the pendant isocyanate on the base polymer of Example I to form a urea linkage.

The graft oligomer 15.96 parts by weight was dissolved in 233.95 parts water and added to a reaction vessel containing the base polymer in acetone. The reaction contents were heated with stirring to reflux until the acetone and water were removed, while simultaneously adding ethyl acetate. The product was recovered as a solution in ethyl acetate.

Example V
Preparation of Macromers for Copolymer in Examples AA–FF

The reaction equipment consisted of a 500 ml reaction vessel equipped with a thermometer, reflux condenser, $N_2$ inlet, and mechanical stirrer. The reaction product was prepared to contain 92.3 pphm (parts per hundred monomer) polybutylene macromer and 7.7 pphm m-TMI: Polybutylene (Kraton HPVM-1201) (28.15 g) and heptane (82.5 g) were charged to the reaction vessel under nitrogen and heated with agitation to relfux at 69° C. Nitrogen flow was discontinued when reflux stated. Meta-TMI (2.36 g) in ethyl acetate (82.5 g) was added in one shot. An IR spectrum was run for an initial reference. Dibutyltin dilaurate (0.2 g) was added in one shot. Reaction contents were heated to reflux until IR spectrum showed completion of reaction. At the completion of the reaction, isopropanol (910.0 g) was added and the contents were heated at reflux for an additional one hour. The reaction product was cooled to room temperature while the reaction vessel was purged with nitrogen. The product was analyzed to be 14.62% active in m-TMI/polybutylene macromer monomer.

This m-TMI/polybutylene macromonomer was substituted for m-TMI and reacted with the monomers reported in Table I for backbone polymers AA–FF according to the procedure of Example I.

Example VI
Preparation of Macromers for Copolymer in Examples GG–JJ

Macromonomers were made according to the procedure of Example V using methacrylato ethyl polystyrenes in place of the polybutylene. The polystyrene was grafted onto the backbone at 6.9 (for GG), 10.0 (for HH) and 16.6 (for JJ) weight percent of the polymer backbone.

Example VII
Compositions and Performance of Graft Copolymers

A series of graft copolymers was prepared according to the procedures outlined in examples I–VI. The compositions, physical properties, and adhesion and cohesion test results are reported in the following tables. The test protocols are recited after the tables. The following abbreviations and tradenames are used in the Tables and have the meanings stated here: BA is butyl acrylate. 2-EHA is 2-ethylhexyl acrylate. MMA is methyl methacrylate. m-TMI is 1-(1-isocyanato-1-methyl ethyl)-3-(1-methyl ethenyl) benzene. MAh is maleic anhydride. AA is acrylic acid. HEA is hydroxy-ethyl acrylate. VAc is vinyl acetate.

Kraton HPVM 1201 is the tradename of a poly(ethylene/butylene) mono-ol, having a linear structure and molecular weight about 3000, and is a product of Shell Chemical company, Houston, Tex. Kraton HPVM 1202 is the tradename of a poly(ethylene/butylene) mono-ol, having a linear structure and molecular weight about 4000, and is a product of Shell Chemical company, Houston, Tex. Jeffamine M2005 is the tradename of a poly(ethyleneoxide/propyleneoxide) monoamine, having a linear structure, a molecular weight of about 2000, and a molar ratio of ethyleneoxide/propyleneoxide of 32:3; it is a product of Huntsman Corporation, Houston, Tex.

In the following examples, the graft polymers V, W, and X were made in 5 Liter batches; examples Y and Z were scaled up reactions to 100 gallons. All of these polymers exhibit very low residual amounts of monomers.

BACKBONE POLYMER COMPOSITION
by Monomer Contents in Wt % and Tg° C.

| BACK-BONE | BA | 2-EHA | MMA | OTHER | FNC. GRP. | Tg |
|---|---|---|---|---|---|---|
| A | 45.5 | 32.5 | 21 | | 1.0 m-TMI | -38 |
| B | 45.5 | 32.5 | 21 | | 1.0 m-TMI | -38 |
| C | 45.5 | 32.5 | 20.4 | | 1.6 m-TMI | -38 |
| D | 45.5 | 32.5 | 21.5 | | 0.5 m-TMI | |
| E | 45.5 | 32.5 | 21 | | 1.0 m-TMI | |
| F | 45.5 | 32.5 | 20 | | 2.0 m-TMI | |
| G | 45.5 | 32.5 | 20.4 | | 1.6 m-TMI | -38 |
| H | 45.5 | 32.5 | 21 | | 1.0 m-TMI | -38 |
| I | 45.5 | 32.5 | 20 | 1 MA | 1.0 m-TMI | -38 |
| J | 44 | 31 | 14.5 | 10 VAc | 0.5 m-TMI | -38 |
| K | 45.5 | 32.5 | 21.5 | | 0.5 m-TMI | -38 |
| L | 45.5 | 32.5 | 21 | | 1.0 m-TMI | -38 |
| M | 45.5 | 32.5 | 20.75 | | 1.25 m-TMI | -38 |
| N | 50 | 49 | 0 | | 1.0 m-TMI | -61 |
| O | 50 | 39 | 10 | | 1.0 m-TMI | -50 |
| P | 44 | 31 | 14 | 10 VAc | 1.0 m-TMI | -38 |
| Q | 45.5 | 32.5 | 21 | | 1.0 m-TMI | -38 |
| R | 45.5 | 32.5 | 21.5 | | 0.5 MAh | |
| S | 45.5 | 32.5 | 21.5 | | 1.0 MAh | |
| T | 45.5 | 32.5 | 21.5 | | 2.0 MAh | |
| U | 45.5 | 32.5 | 21 | | 1 m-TMI | -38 |
| V | 45.5 | 32.5 | 20.5 | | 1.45 m-TMI | -38 |
| W | 45.5 | 32.5 | 20.5 | amino-butanol | 1.45 m-TMI | -38 |
| X | 45.5 | 32.5 | 20.5 | | 1.45 m-TMI | -38 |
| Y | 45.5 | 32.5 | 20.5 | | 1.45 m-TMI | -38 |
| Z | 45.5 | 32.5 | 20.5 | amino-butanol | 1.45 m-TMI | -38 |
| AA | 50.2 | 35.9 | 5.5 | 6.7 AA | 1.7 HEA | -48 |
| BB | 50.2 | 35.9 | 5.5 | 6.7 AA | 1.7 HEA | -48 |
| CC | 50.2 | 35.9 | 5.5 | 6.7 AA | 1.7 HEA | -48 |
| DD | 50.2 | 35.9 | 5.5 | 6.7 AA | 1.7 HEA | -48 |
| EE | 50.2 | 35.9 | 5.5 | 6.7 AA | 1.7 HEA | -48 |
| FF | 50.2 | 35.9 | 5.5 | 6.7 AA | 1.7 HEA | -48 |

GRAFT COPOLYMERS

| BACKBONE | MACROMER | GRAFT RATE | GRAFT WT % | $M_W/M_N$ | SKIN TEST |
|---|---|---|---|---|---|
| A | Kraton 1202 | 1 | 16.6 | 10.6 | 3.7 |
| B | Kraton 1202 | 1 | 15.9 | 7.3 | 4.0 |
| C | Kraton 1201 | 1.6 | 13.0 | 5.9 | 4.0 |
| D | Kraton 1201 | | | | 6.3 |
| E | Kraton 1201 | | | | 5.0 |
| F | Kraton 1201 | | | | 4.7 |
| G | Kraton 1201 | 1.6 | 6.9 | 8.5 | 6.3 |
| H | Kraton 1201 | 1.0 | 13 | 15 | 4.7 |
| I | Kraton 1201 | 1.0 | 13 | | 6.7 |
| J | Kraton 1202 | 0.5 | 8.7 | 5.83 | 5.0 |
| K | Kraton 1201 | 0.5 | 6.9 | 9.7 | 5.3 |
| L | Kraton 1201 | 1.0 | 13.0 | 11.2 | 6.0 |
| M | Kraton 1201 | 1.25 | 13.0 | 10.4 | 5.7 |
| N | Kraton 1201 | 1.0 | 13 | 30.8 | 7.0 |
| O | Kraton 1201 | 1.0 | 13 | 18.3 | 7.0 |
| P | Kraton 1201 | 0.37 | 7.2 | 6.1 | 7.0 |
| Q | Saccharide | 1.0 | 8.5 | 21.6 | 4.3 |
| R | Jeffamine 2005 | 1.0 | 9.3 | 8.4 | 6.0 |
| S | Jeffamine 2005 | 1.0 | 9.3 | | 5.0 |
| T | Jeffamine 2005 | 1.0 | 9.3 | | 4.7 |
| U | Jeffamine 2005 | 1.0 | 9 | 5.4 | 7.0 |
| V | Kraton 1202 | 0.75 | 13 | 11.9 | |
| W | Kraton 1202 | 0.75 | 6.9 | | |
| X | Jeffamine 2005 | 1.0 | 9 | | |
| Y | Kraton 1202 | 0.75 | 13 | 11.7 | |
| Z | Kraton 1202 | 0.75 | 6.9 | 12.2 | |
| AA | Kraton 1202 m-TMI | 0.37 | 7.2 | 13.7 | 7.0 |
| BB | Kraton 1202 m-TMI | 0.37 | 7.2 | | 5.0 |
| CC | Kraton 1202 m-TMI | 0.37 | 7.2 | | 4.3 |
| DD | Kraton 1202 m-TMI | 0.63 | 10 | 10.6 | 6.7 |
| EE | Kraton 1202 m-TMI | 0.63 | 10 | | 6.3 |
| FF | Kraton 1202 m-TMI | 0.63 | 10 | | 6.0 |

RESIDUAL MONOMER CONTENT
in Graft Copolymer in PPM

| BACK-BONE | BA | 2-EHA | MMA | OTHER | FNC. GRP.* | Total ppm |
|---|---|---|---|---|---|---|
| A | 89 | 11 | 29 | | | 129 |
| B | 481 | | 78 | | | 559 |
| I | 101 | 42 | <20 | | | 163 |
| K | 1064 | 717 | <10 | | | 1791 |
| L | 694 | 446 | <10 | | | 1150 |
| M | 1108 | 472 | <10 | | | 1590 |
| O | 682 | 478 | 26 | | | 1186 |
| V | 460 | 323 | <50 | | | 833 |
| W | 1384 | 970 | <50 | | | 2404 |
| X | 675 | 490 | <50 | | | 1215 |
| Y | 520 | 320 | <50 | | | 890 |
| Z | 440 | 255 | <50 | | | 745 |

* Monomer containing additional functional group for reacting in condensation reaction with polymer to be grafted.

Comparative Example VII

Compositions and Performance of Comparative Graft Copolymers

Three graft copolymers, designated comparative examples GG, HH, and JJ, were prepared with a polymer backbone having the same monomer composition of backbone polymer AA and grafted moieties of the commercially available polystyrene methacrylate macromer having a molecular weight of 4000, distributed by Sartomer Company, Inc., Exton, Pa. The polystyrene was grafted onto the backbone at 6.9 (for GG), 10.0 (for HH) and 16.6 (for JJ) weight percent of the polymer backbone. The comparative graft copolymers were tested according to the skin adhesion protocol below, and none achieved a rating greater than 5. The skin test values and total residual monomer counts for each were as follows:

| Copolymer | Skin Test | Total Residual Monomer |
|---|---|---|
| GG | 5 | 3842 ppm |
| HH | 4 | 3390 ppm |
| JJ | 1.5 | 3982 ppm |

The above examples show that the inventive graft copolymers as a group provide better skin testing results than the polystyrene graft copolymers.

Comparative Example VIII
Water Vapor Transmission Rates

Several of the copolymers in the Examples above were tested for water vapor transmission rate according to the protocol given below. The results are reported in grams/m$^2$/24 hours and show that the polyethylene/polypropylene oxide sample, marked with an asterisk in the data below, demonstrated superior transmission rates compared to the polybutylene, polystyrene and polysaccharide graft copolymers:

| Graft Copolymer | U | Q | Y | Z | GG | HH | JJ |
|---|---|---|---|---|---|---|---|
| WVTR | 1349* | 395 | 351 | 349 | 545 | 526 | 265 |

INDUSTRIAL UTILITY

The described graft copolymers can be used as adhesives in medical devices such as transdermal patches or wound dressings. Typically, these patches or dressings contain an active medicament, either contained in the same layer as the adhesive or in a spatial relationship.

TEST PROTOCOLS

The following protocols were used to obtain the values in the above tables.

Preparation of a Transdermal Patch. For each graft copolymer, a transdermal patch was constructed by sequentially applying the following layers to a silicon coated paper: (a) a one mil thick coating of the graft copolymer blended with 1% by weight of a metal acetylacetonate (typically titanium or aluminum) crosslinker; (b) a microporous polypropylene (such as sold under the tradename Cellguard by Hoechst Celanese); (c) a film prepared by the coextrusion of an ethylene/vinyl acetate copolymer with the desired enhancer to act as a reservoir for the enhancer; (d) an impenetrable polyester, to assure that the enhancer migrates toward the adhesive; and (e) an effective amount of a weight to assure intimate contact of the above layers. The enhancer is present in the coextruded ethylene/vinyl acetate copolymer in an amount in excess of what could be absorbed by the adhesive. Each patch was allowed to equilibrate in the enhancer at 37° C. for two weeks. The patches were then conditioned at 22.5° C. and 50% relative humidity for one hour. The release liner was removed and the exposed adhesive adhered to stainless steel panels or to skin for adhesion and cohesion testing.

Skin Adhesion. The graft copolymers, within the transdermal patch, individually were tested by a panel of three people. The patch was applied with finger pressure to the back of the hand, after the hand was washed with mild soap and dried. The patch was allowed to remain for approximately two minutes, and then pulled off by hand. The force required to remove the patch was rated as low, medium, or high, or as a minus or plus of those ratings. Each of those ratings was assigned a numerical value according to the following schedule: low minus equaled one, low equaled two, low plus equaled three, medium minus also equaled three, medium equaled four, medius plus equaled five, high minus also equaled five, high Equaled six, and high plus equaled seven. Each panelist tested each adhesive patch one time, and the results from all three panelists for each adhesive were pooled and averaged.

Water Vapor Transmission Rate. A one mil coating of the adhesive on release liner is transferred to a macropouous cotton cheese cloth (pores approx. 1mm). The cloth with adhesive is placed on a 8.8 cm diameter petri dish with the side of cheese cloth without the adhesive facing the atmosphere. A small opening is left to inject distilled water into the petri dish and sufficient water is added to cover the entire bottom surface of the petri dish without touching the adhesive. The opening is sealed using the adhesive and this set-up is first weighed and then stored in a controlled temperature and humidity room (22° C. and 50% RH) for 24 hours. The dish is weighed again and the weight loss expressed in terms of grams of water lost per square meter in the 24 hour period.

We claim:

1. A graft copolymer comprising a backbone polymer to which are grafted amine terminated polysaccharide polymeric moieties, the graft copolymer characterized in that (i) the backbone polymer is a pressure sensitive polymer having a glass transition temperature of –30° C. or less prepared from acrylic, methacrylic and vinyl monomers, and (ii) the grafted polymeric moieties absorb less than 10% by weight of the skin-penetration enhancer under thermodynamic equilibrium at 25° C. when introduced into an excess of the enhancer independently from the backbone polymer.

2. A drug delivery patch or dressing containing a pressure sensitive adhesive comprising the graft copolymer of claim 1.

* * * * *